(12) United States Patent
Saeidi et al.

(10) Patent No.: US 12,156,708 B2
(45) Date of Patent: Dec. 3, 2024

(54) CONFIDENCE-BASED ROBOTICALLY-ASSISTED SURGERY SYSTEM

(71) Applicants: University of Maryland, College Park, College Park, MD (US); The Johns Hopkins University, Baltimore, MD (US); Children's National Medical Center, Washington, DC (US)

(72) Inventors: Hamed Saeidi, College Park, PA (US); Axel Krieger, Alexandria, VA (US); Simon Leonard, State College, PA (US); Justin Opfermann, Washington, DC (US)

(73) Assignees: UNIVERSITY OF MARYLAND, COLLEGE PARK, College Park, MD (US); THE JOHN HOPKINS UNIVERSITY, Baltimore, MD (US); CHILDREN'S NATIONAL MEDICAL CENTER, Washington, DC (US)

( * ) Notice: Subject to any disclaimer, the term of this patent is extended or adjusted under 35 U.S.C. 154(b) by 779 days.

(21) Appl. No.: 17/054,960

(22) PCT Filed: May 16, 2019

(86) PCT No.: PCT/US2019/032635
§ 371 (c)(1),
(2) Date: Nov. 12, 2020

(87) PCT Pub. No.: WO2019/222480
PCT Pub. Date: Nov. 21, 2019

(65) Prior Publication Data
US 2021/0205032 A1    Jul. 8, 2021

Related U.S. Application Data

(60) Provisional application No. 62/672,485, filed on May 16, 2018.

(51) Int. Cl.
*A61B 34/30* (2016.01)
*A61B 17/32* (2006.01)
(Continued)

(52) U.S. Cl.
CPC .............. *A61B 34/30* (2016.02); *A61B 17/32* (2013.01); *A61B 34/25* (2016.02); *A61B 34/32* (2016.02);
(Continued)

(58) Field of Classification Search
CPC ......... A61B 34/30; A61B 17/32; A61B 34/25; A61B 34/32; A61B 34/74; A61B 18/14;
(Continued)

(56) References Cited

U.S. PATENT DOCUMENTS

| 4,604,787 A | 8/1986 | Silvers, Jr. |
| 5,111,590 A | 5/1992 | Park |

(Continued)

FOREIGN PATENT DOCUMENTS

| WO | 2012018816 A2 | 2/2012 |
| WO | 2014005139 A2 | 1/2014 |

(Continued)

OTHER PUBLICATIONS

USPTO, PCT International Search Report and Written Opinion, PCT/US2019/032635, Jul. 29, 2019.

(Continued)

*Primary Examiner* — Jason Holloway
(74) *Attorney, Agent, or Firm* — Quarles & Brady LLP

(57) ABSTRACT

The present disclosure provides a system and method for controlling an articulating member including a tool. The method includes determining a first confidence indicator based on a manual control mode for the articulating member, determining a second confidence indicator based on an autonomous control mode for the articulating member, gen- (Continued)

erating an allocation function based on the first confidence indicator and the second confidence indicator, and generating a control command for the articulating member based on the allocation function.

18 Claims, 12 Drawing Sheets

(51) Int. Cl.
    *A61B 34/00*     (2016.01)
    *A61B 34/32*     (2016.01)
    *B25J 9/16*     (2006.01)
    *A61B 18/00*     (2006.01)
    *A61B 18/14*     (2006.01)

(52) U.S. Cl.
    CPC .............. *A61B 34/74* (2016.02); *B25J 9/1653* (2013.01); *B25J 9/1689* (2013.01); *A61B 2018/00595* (2013.01); *A61B 18/14* (2013.01); *A61B 2018/1425* (2013.01); *A61B 34/76* (2016.02)

(58) Field of Classification Search
    CPC .......... A61B 34/76; A61B 2018/00595; A61B 2018/1425; A61B 2090/065; B25J 9/1653; B25J 9/1689; B25J 9/163; B25J 9/1697

See application file for complete search history.

(56) References Cited

U.S. PATENT DOCUMENTS

| | | | |
|---|---|---|---|
| 6,325,808 B1 * | 12/2001 | Bernard | A61B 34/30 606/139 |
| 7,164,968 B2 | 1/2007 | Treat et al. | |
| 7,831,292 B2 | 11/2010 | Quaid et al. | |
| 8,718,372 B2 | 5/2014 | Holeva et al. | |
| 9,220,570 B2 | 12/2015 | Kim et al. | |
| 9,788,903 B2 | 10/2017 | Kim et al. | |
| 9,805,306 B1 | 10/2017 | Bataller et al. | |
| 10,864,640 B1 | 12/2020 | Innes et al. | |
| 2005/0154295 A1 | 7/2005 | Quistgaard et al. | |
| 2009/0326713 A1 | 12/2009 | Moriya | |
| 2011/0202068 A1 | 8/2011 | Diolaiti et al. | |
| 2014/0039517 A1 | 2/2014 | Bowling et al. | |
| 2015/0223683 A1 | 8/2015 | Davidovics et al. | |
| 2016/0000631 A1 | 1/2016 | Becker | |
| 2016/0058517 A1 * | 3/2016 | Kim | A61B 34/30 606/130 |
| 2016/0161444 A1 | 6/2016 | Shimizu et al. | |
| 2017/0249844 A1 | 8/2017 | Perkins et al. | |
| 2018/0193099 A1 | 7/2018 | Kim et al. | |
| 2019/0001380 A1 | 1/2019 | Amaiwa | |
| 2021/0315637 A1 * | 10/2021 | Ida | A61B 34/30 |
| 2022/0383531 A1 * | 12/2022 | Santini | H04N 13/239 |
| 2023/0054209 A1 * | 2/2023 | Roh | A61B 34/76 |

FOREIGN PATENT DOCUMENTS

| | | |
|---|---|---|
| WO | 2014121262 A2 | 8/2014 |
| WO | 2018209042 A2 | 11/2018 |

OTHER PUBLICATIONS

Sucan, I. et al., The Open Motion Planning Library, IEEE Robotics & Automation Magazine, 2012, 19(4):72-82.
Tirelli, G. et al., NBI Utility in the Pre-Operative and Intra-Operative Assessment of Oral Cavity and Oropharyngeal Carcinoma, American Journal of Otolaryngology, 2017, 38(1):65-71.
Van Der Merwe, R. et al., The Unscented Particle Filter, Advances in Neural Information Processing Systems, 2001, pp. 584-590.
Vicini, C. et al., A Novel Approach Emphasising Intra-Operative Superficial Margin Enhancement of Head-Neck Tumours with Narrow-Band Imaging in Transoral Robotic Surgery, Acta Otorhinolaryngologica Italica, 2015, 35:157-161.
Wan, E. et al., The Unscented Kalman Filter for Nonlinear Estimation, Proceedings of the IEEE 2000 Adaptive Systems for Signal Processing, Communications, and Control Symposium (Cat. No.00EX373), Oct. 2000, pp. 153-158.
Wu, T. et al., Optical Imaging for Medical Diagnosis Based on Active Stereo Vision and Motion Tracking, Optics Express, 2007, 15(16):10421-10426.
Wu, C. et al., In-Vivo Optical Imaging in Head and Neck Oncology: Basic Principles, Clinical Applications and Future Directions, International Journal of Oral Science, 2018, 10(2):1-13.
Xia, T. et al., An Integrated System for Planning, Navigation and Robotic Assistance for Skull Base Surgery, Int. J. Med. Robot., 2008, 4(4):321-330.
Yip, M. et al., Chapter 1, Robot Autonomy for Surgery, Encyclopedia of Medical Robotics, 2017, 1:281-313.
Zhou, X. et al., Path Planning for Robot-Enhanced Cardiac Radiofrequency Catheter Ablation, IEEE International Conference on Robotics and Automation, 2016, pp. 4172-4177.
PCT International Search Report and Written Opinion, PCT/US2020/033270, Jul. 17, 2020, 9 pages.
Alemzadeh, H. et al., Adverse Events in Robotic Surgery: a Retrospective Study of 14 Years of FDA Data, PLoS One, 2016, 11(4):e0151470, pp. 1-20.
Alexa, M. et al., Computing and Rendering Point Set Surfaces, IEEE TVCG, 2003, 9(1):1-12.
Anderson, C. et al., A Meta-Analysis of Margin Size and Local Recurrence in Oral Squamous Cell Carcinoma, Oral Oncology, 2015, 51(5):464-469.
Bargar, W. et al., Primary and Revision Total Hip Replacement Using the Robodoc(R) System, Clinical Orthopaedics and Related Research, 1998, 354:82-91.
Baumhauer, M. et al., Navigation in Endoscopic Soft Tissue Surgery: Perspectives and Limitations, Journal of Endourology, 2008, 22(4):751-766.
Beck, F. et al., tuw_checkerboard, http://wiki.ros.org/tuw_checkerboard, Version dated Oct. 20, 2018, Accessed online at https://web.archive.org/web/20181020082321/http://wiki.ros.org/tuw_checkerboard, 3 pages.
Bodner, J. et al., First Experiences with the da Vinci(TM) Operating Robot in Thoracic Surgery, European Journal of Cardio-Thoracic Surgery, 2004, 25(5):844-851.
Colas, F. et al., 3D Path Planning and Execution for Search and Rescue Ground Robots, IEEE/RSJ Int. Conf. on Intelligent Robots and Systems, 2013, pp. 722-727.
Coulson, C. et al., An Autonomous Surgical Robot for Drilling a Cochleostomy: Preliminary Porcine Trial, Clinical Otolaryngology, 2008, 33:343-347.
Decker, R. et al., A Biocompatible Near-Infrared 3D Tracking System, IEEE Trans. Biomed. Eng., 2017, 64 (3):549-556.
Dijkstra, E., A Note on Two Problems in Connexion with Graphs, Numerische Mathematik, 1959, 1:269-271.
Ferlay, J. et al., Cancer Incidence and Mortality Worldwide: Sources, Methods and Major Patterns in Globocan 2012, International Journal of Cancer, 2015, 136(5):E359-E386.
Fu, T. et al., The Role of Transoral Robotic Surgery, Transoral Laser Microsurgery, and Lingual Tonsillectomy in the Identification of Head and Neck Squamous Cell Carcinoma of Unknown Primary Origin: a Systematic Review, Journal of Otolaryngology—Head & Neck Surgery, 2016, 45:28, pp. 1-10.
Fullum, T. et al., Comparison of the Clinical and economic Outcomes Between Open and Minimally Invasive Appendectomy and Colectomy: Evidence from a Large Commercial Payer Database, Surgical Endoscopy, 2010, 24 (4):845-853.
Haidegger, T., Autonomy for Surgical Robots: Concepts and Paradigms, IEEE Transactions on Medical Robotics and Bionics, 2019, 1(2):65-76.
Hennersperger, C. et al., Towards MRI-Based Autonomous Robotic US Acquisitions: a First Feasibility Study, IEEE Transactions on Medical Imaging, 2017, 36(2):538-548.

(56) References Cited

OTHER PUBLICATIONS

Hu, D. et al., Semi-Autonomous Image-Guided Brain Tumor Resection Using an Integrated Robotic System: a Bench-Top Study, International Journal of Medical Robotics, 2018, 14(1):e1872, 40 pages.

Huang, S. et al., Oral Cancer: Current Role of Radiotherapy and Chemotherapy, Med Oral Patol Oral Cir Buscal, 2013, 18(2):e233-e240.

Jackson, R. et al., Needle Path Planning for Autonomous Robotic Surgical Suturing, IEEE International Conference on Robotics and Automation, 2013, 2013: 1669-1675.

Jackson, R. et al., Needle-Tissue Interaction Force State Estimation for Robotic Surgical Suturing, IEEE/RSJ International Conference on Intelligent Robots and Systems (IROS), 2016, pp. 3659-3664.

Jackson, R. et al., Real-Time Visual Tracking of Dynamic Surgical Suture Threads, IEEE Trans Autom Sci Eng, 2018, 15(3):1078-1090.

Kazanzides, P. et al., An Integrated System for Cementless Hip Replacement, IEEE Engineering in Medicine and Biology Magazine, 1995, 14(3):307-313.

Knoll, A. et al., Selective Automation and Skill Transfer in Medical Robotics: a Demonstration on Surgical Knot-Tying, International Journal of Medical Robotics and Computer Assisted Surgery, 2012, 8:384-397.

Lavalle, S. et al., Randomized Kinodynamic Planning, International Journal of Robotics Research, 2001, 20 (5):378-400.

Le, H. et al., Experimental Assessment of a 3-D Plenoptic Endoscopic Imaging System, Chin Opt Lett, 2017, 15(5), 15 pages.

Le, H. et al., Semi-Autonomous Laparoscopic Robotic Electro-Surgery with a Novel 3D Endoscope, IEEE International Conference on Robotics and Automation, 2018, 2018:6637-6644.

Leonard, S. et al., Smart Tissue Anastomosis Robot (STAR): a Vision-Guided Robotics System for Laparoscopic Suturing, IEEE Transactions on Biomedical Engineering, 2014, 61(4):1305-1317.

Leonard, S. et al., Smart Tissue Anastomosis Robot (STAR): Accuracy Evaluation for Supervisory Suturing Using Near-Infrared Fluorescent Markers, IEEE International Conference on Robotics & Automation, 2014, pp. 1889-1894.

Liu, M., Robotic Online Path Planning on Point Cloud, IEEE Transactions on Cybernetics, 2016, 46(5):1217-1228.

Liu, S. et al., Preoperative Surgical Planning for Robot-Assisted Liver Tumor Ablation Therapy Based on Collision-Free Reachable Workspaces, International Journal of Robotics and Automation, 2017, 32(5):440-457.

Marchand, E. et al., ViSP for Visual Servoing: a Generic Software Platform with a Wide Class of Robot Control Skills, IEEE Robotics and Automation Magazine, 2005, 12(4):40-52.

Marescaux, J. et al., Next Step in Minimally Invasive Surgery: Hybrid Image-Guided Surgery, Journal of Pediatric Surgery, 2015, 50(1):30-36.

Mercante, G. et al., Transoral Robotic Surgery (TORS) for Tongue Base Tumours, Acta Otorhinolaryngologica Italica, 2013, 33(4):230-235.

Newcombe, R. et al., DynamicFusion: Reconstruction and Tracking of Non-Rigid Scenes in real-Time, Proceedings of the IEEE Conference on Computer Vision and Pattern Recognition, 2015, pp. 343-352.

Opfermann, J. et al., Semi-autonomous Electrosurgery for Tumor Resection Using a Multi-Degree of Freedom Electrosurgical Tool and Visual Servoing, Int. Conf. Intell. Robots and Sys., 2017, pp. 3653-3660.

Quigley, M. et al., ROS: An Open-Source Robot Operating System, ICRA Workshop on Open Source Software, 2009, vol. 3, 6 pages.

Reflexxes. Reflexxes Motion Libraries, Version dated Sep. 20, 2018, http://web.archive.org/web/20180920075318/http://www.reflexxes.ws/reflexxes-motion-libraries-details.html, 2 pages.

Rosten, E. et al., Fusing Points and Lines for High Performance Tracking, Tenth IEEE International Conference on Computer Vision (ICCV'05), 2005, 2:1508-1515.

Rusu, R. et al., 3D is Here: Point Cloud Library (PCL), IEEE International Conference on Robotics and Automation, 2011, pp. 1-4.

Saeidi, H. et al., A Mixed-Initiative Haptic Teleoperation Strategy for Mobile Robotic Systems Based on Bidirectional Computational Trust Analysis, IEEE Transactions on Robotics, 2017, 33(6): 1500-1507.

Saeidi, H. et al., A Confidence-Based Shared Control Strategy for the Smart Tissue Autonomous Robot (STAR), 2018 IEEE/RSJ International Conference on Intelligent Robots and Systems (IROS), 2018, pp. 1268-1275.

Saeidi, H. et al., Autonomous Laparoscopic Robotic Suturing with a Novel Actuated Suturing Tool and 3D Endoscope, IEEE International Conference on Robotics and Automation, 2019, 2019:1541-1547.

Salman, M. et al., Use, Cost, Complications, and Mortality of Robotic Versus Nonrobotic General Surgery Procedures Based on a Nationwide Database, The American Surgeon, 2013, 79(6):553-560.

Schnabel, R. et al., Efficient Ransac for Point-Cloud Shape Detection, Computer Graphics Forum, 2007, 26 (2):214-226.

Shademan, A. et al., Feasibility of Near-Infrared Markers for Guiding Surgical Robots, Optical Modeling and Performance Predictions VI, Proc. of SPIE, 2013, vol. 8840, 10 pages.

Shademan, A. et al., Supervised Autonomous Robotic Soft Tissue Surgery, Science Translational Medicine, 2016, 8 (337):108.

Sinclair, D., S-hull: A Fast Radial Sweep-Hull Routine for Delaunay Triangulation, arXiv: 1604.01428, 2016, pp. 1-7.

Smits, R., KDL: Kinematics and Dynamics Library, Published Feb. 25, 2010, http:/web.archive.org/web/20201128223717/https://www.orocos.org/kdl/release-102.html, 1 page.

Stephan, D. et al., First Experiences with the New Senhance(R) Telerobotic System in Visceral Surgery, Visceral Medicine, 2018, 34(1):31-36.

Stewart, C. et al., Robotic Surgery Trends in General Surgical Oncology from the National Inpatient Sample, Surgical Endoscopy, 2019, 33(8):2591-2601.

* cited by examiner

_US 12,156,708 B2_

CONFIDENCE-BASED ROBOTICALLY-ASSISTED SURGERY SYSTEM

STATEMENT REGARDING FEDERALLY SPONSORED RESEARCH

This invention was made with government support under R01 EB020610, and R21 EB024707 awarded by the National Institutes of Health. The government has certain rights in the invention.

TECHNICAL FIELD

The present disclosure relates to a system. More particularly, the present disclosure relates to a robotically-assisted surgery (RAS) system.

BACKGROUND

The field of medical robotics has dramatically evolved over the past two decades due to advances in robotic and camera technology, and sales of medical robots were estimated at US$1.61 billion in 2016. RAS systems are based on teleoperation (i.e., remote operation or operation at a distance), and include robots, cameras, highly dexterous surgical tools, etc. Many RAS systems provide a minimally invasive surgery (MIS) approach, which can be faster, safer and require less patient recovery time. Additionally, a RAS system can reduce human errors and improve patient outcomes by leveraging robotic accuracy and repeatability during certain surgical procedures. However, a completely autonomous RAS system is still not feasible for many surgical situations, procedures and environments.

DETAILED DESCRIPTION

Figure 1:
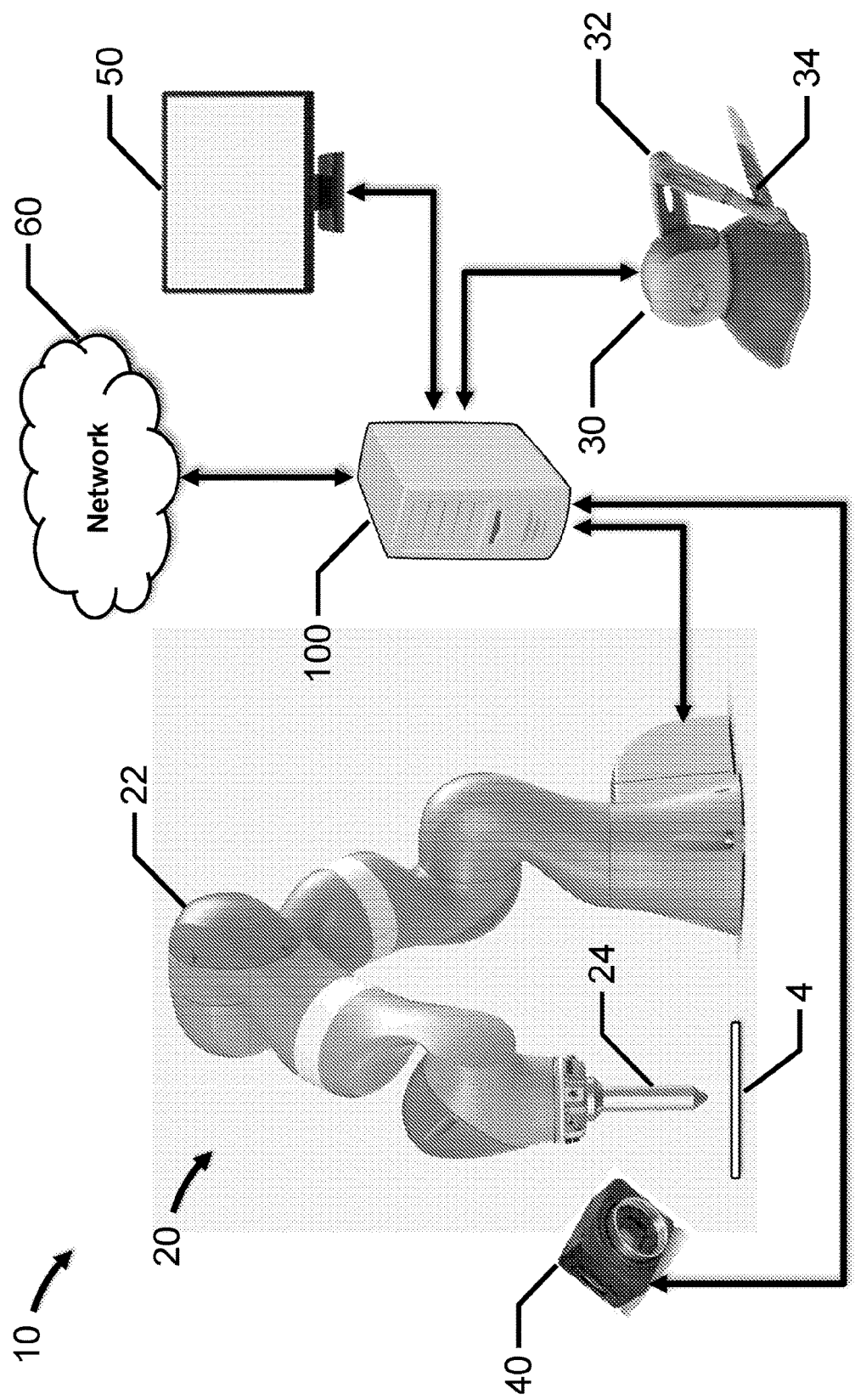
FIG. 1 depicts a schematic diagram of a RAS system, in accordance with an embodiment of the present disclosure.

Embodiments of the present disclosure will now be described with reference to the drawing figures, in which like reference numerals refer to like parts throughout.

Embodiments of the present disclosure advantageously improve both RAS system efficiency and patient outcomes by combining the best features of automation with the complementary skills of the surgeon operating the RAS system. While automation of the RAS system may provide greater accuracy and repeatability in certain surgical situations, automation is not infallible and safe operation requires surgeon supervision and possible intervention. Accordingly, the present disclosure provides a control system that allows surgical procedures to be performed collaboratively between robot and surgeon with the highest possible degree of autonomy, while ensuring safe operation at all times.

More particularly, embodiments of the present disclosure provide a confidence-based shared control system that provides an automated control allocation during a surgical task, situation, procedure, etc. Importantly, the confidence-based shared control system improves the surgical performance of any surgeon by reducing not only the overall error committed by the surgeon, but also the workload of the surgeon during the task.

FIG. 1 depicts a schematic diagram of RAS system 10, in accordance with an embodiment of the present disclosure.

RAS system 10 includes computer 100 coupled to robot 20, input device 30, camera 40 and display 50. Tissue 4 may include one or more tissue samples, a region of interest of a patient, etc. Robot 20 includes articulated member or arm 22 and tool 24. Generally, tool 24 is an extension of arm 22, and may be, for example, a surgical tool, an electro-surgical tool, a laser, etc. The movement of tool 24 is controlled by commands to robot 20. Input device 30 includes stylus 32 and one or more switches or buttons 34. Computer 100 may also be coupled to network 60, which may include one or more local area networks, wide area networks, the Internet, etc.

In one embodiment, robot 20 is a Smart Tissue Autonomous Robot (STAR) that includes a KUKA LBR iiwa robot with a 7-DOF (degree of freedom) lightweight arm 22 and a surgical tool 24. Robot 20 receives control commands or signals from computer 100, and sends positional information for arm 22 to computer 100. The control commands or signals may include one or more of the following types of data: position, velocity, acceleration, force, torque, etc.

In one embodiment, surgical tool 24 is an electro-cautery tool that is based on a 2-DOF laparoscopic grasper Radius T manufactured by Tuebingen Scientific. Electro-cautery tool 24 includes a shaft, a quick release interface that is electrically isolated from the shaft, and two conductors, disposed within the center of electro-cautery tool 24, that are electrically coupled to an electro-surgical generator (ESG) (not depicted for clarity). In operation, a needle electrode is inserted into the quick-release interface, and a cutting waveform is selected on the ESG. When the surgeon activates an input control for the ESG, such as, for example, a foot pedal, a button or switch, etc., the ESG receives a control signal. In response, the ESG generates an electrical signal representing the cutting waveform, and then sends the electrical signal to the needle electrode. A grounding pad, disposed underneath the tissue sample, patient, etc. in task space 2, is coupled to the ESG to complete the electrical circuit. The electrical signal vaporizes tissue in contact with the electrode, thereby cutting the tissue. Alternatively, computer 100 may receive the ESG control signal from input device 30, and then send the ESG control signal to the ESG. For example, input device 30 may include a button or switch that is mapped to the ESG control signal. Alternatively, input device 30 may be coupled to the ESG and provide the ESG control signal directly thereto.

Other embodiments of robot 20, including different arms 22 and tools 24, are also contemplated, such as, for example, a motorized suturing device, etc. In one embodiment, input device 30 is a 6-DOF Sensable Technologies Phantom Omni haptic device 30 that allows the surgeon to manually control robot 20. In this embodiment, haptic device 30 sends positional information for stylus 32 and commands received through buttons 34 to computer 100, and may receive haptic feedback from computer 100. If haptic feedback is provided, haptic device 30 includes one or more haptic actuators that render the haptic feedback to the surgeon. Haptic feedback may include force, vibration, motion, texture, etc. Other embodiments of input device 30 are also contemplated.

In one embodiment, camera 40 is a Point Grey Chameleon RGB (red green blue) camera. Camera 40 sends image data to computer 100 that provide visual feedback to the surgeon and input data for the autonomous control mode discussed below. Other embodiments of camera 40 are also contemplated.

Figure 2:
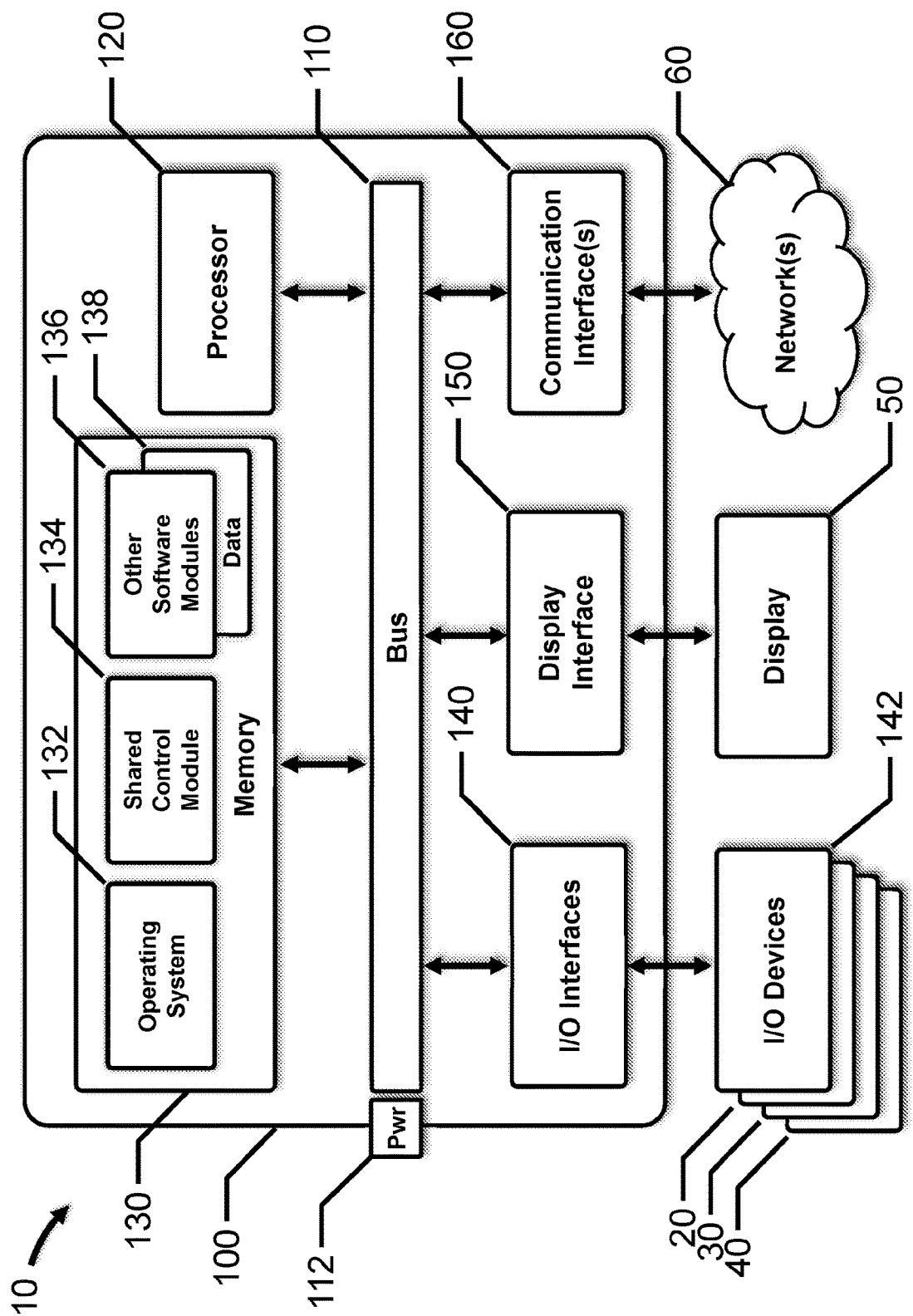
FIG. 2 depicts a block diagram of the RAS system depicted in FIG. 1, in accordance with an embodiment of the present disclosure.

FIG. 2 depicts a block diagram of RAS system 10 depicted in FIG. 1, in accordance with an embodiment of the present disclosure.

Computer 100 includes bus 110, processor 120, memory 130, I/O interfaces 140, display interface 150, and one or more communication interfaces 160. Generally, I/O interfaces 140 are coupled to I/O devices 142 using a wired or wireless connection, display interface 150 is coupled to display 50, and communication interface 160 is connected to network 60 using a wired or wireless connection.

Bus 110 is a communication system that transfers data between processor 120, memory 130, I/O interfaces 140, display interface 150, and communication interface 160, as well as other components not depicted in FIG. 1. Power connector 112 is coupled to bus 110 and a power supply (not shown).

Processor 120 includes one or more general-purpose or application-specific microprocessors to perform computation and control functions for computer 100. Processor 120 may include a single integrated circuit, such as a microprocessing device, or multiple integrated circuit devices and/or circuit boards working in cooperation to accomplish the functions of processor 120. In addition, processor 120 may execute computer programs or modules, such as operating system 132, shared control module 134, other software modules 136, etc., stored within memory 130.

Memory 130 stores information and instructions for execution by processor 120. Generally, memory 130 may include a variety of non-transitory computer-readable medium that may be accessed by processor 120. In various embodiments, memory 130 may include volatile and nonvolatile medium, non-removable medium and/or removable medium. For example, memory 130 may include any combination of random access memory ("RAM"), dynamic RAM (DRAM), static RAM (SRAM), read only memory ("ROM"), flash memory, cache memory, and/or any other type of non-transitory computer-readable medium.

Memory 130 contains various components for retrieving, presenting, modifying, and storing data. For example, memory 130 stores software modules that provide functionality when executed by processor 120. The software modules include an operating system 132 that provides operating system functionality for computer 100. The software modules also include shared control module 134 that provides functionality for controlling robot 20. In certain embodiments, shared control module 134 may include a plurality of modules, each module providing specific individual functionality for controlling robot 20. Other software modules 136 may cooperate with shared control module 134 to provide functionality for controlling robot 20, such as planning algorithms, robot controllers, computer vision, control allocation strategies, etc.

In certain embodiments, other software modules 136 may include a Robot Operating System (ROS), which provides a flexible collection of tools, libraries, device drivers, such as robot device drivers, sensor device drivers, etc., conventions, etc. For example, other software modules 136 may include an OpenCV (Open Source Computer Vision) library that provides a common infrastructure for computer vision applications, one or more Reflexxes Motion Libraries that provide instantaneous trajectory generation capabilities for motion control systems, a Kinematics and Dynamics Library (KDL) in Open Robot Control Systems (OROCOS) that provides an application independent framework for modelling and computation of kinematic chains for robots, etc.

Data 138 may include data associated with operating system 132, shared control module 134, other software modules 136, etc.

I/O interfaces 140 are configured to transmit and/or receive data from I/O devices 142. I/O interfaces 140 enable connectivity between processor 120 and I/O devices 142 by encoding data to be sent from processor 120 to I/O devices 142, and decoding data received from I/O devices 142 for processor 120. Generally, data may be sent over wired and/or a wireless connections. For example, I/O interfaces 140 may include one or more wired communications interfaces, such as USB, Ethernet, etc., and/or one or more wireless communications interfaces, coupled to one or more antennas, such as WiFi, Bluetooth, cellular, etc.

Generally, I/O devices 142 provide input to computer 100 and/or output from computer 100. As discussed above, I/O devices 142 are operably connected to computer 100 using either a wireless connection or a wired connection. I/O devices 142 may include a local processor coupled to a communication interface that is configured to communicate with computer 100 using the wired or wireless connection. For example, I/O devices 142 include robot 20, input device 30, camera 40, and may include other devices, such as a joystick, keyboard, touch pad, etc.

Display interface 150 is configured to transmit image data from computer 100 to monitor or display 50.

Communication interface 160 is configured to transmit data to and from network 60 using one or more wired or wireless connections. Network 60 may include one or more local area networks, wide area networks, the Internet, etc., which may execute various network protocols, such as, for example, wired and wireless Ethernet, Bluetooth, etc. Network 60 may also include various combinations of wired and/or wireless physical layers, such as, for example, copper wire or coaxial cable networks, fiber optic networks, Bluetooth wireless networks, WiFi wireless networks, CDMA, FDMA and TDMA cellular wireless networks, etc.

Figure 3A:
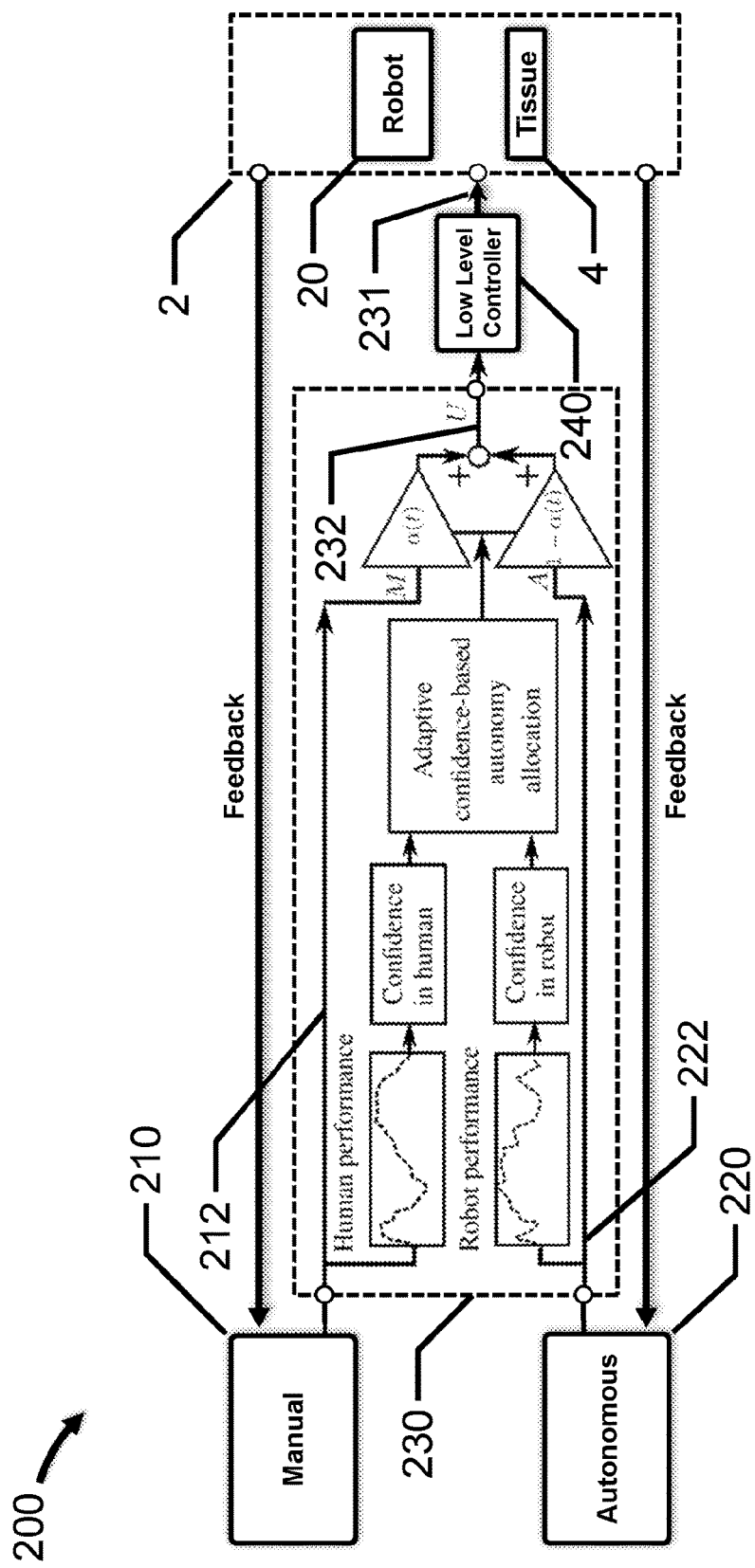
FIG. 3A depicts a block diagram of a shared control system, in accordance with an embodiment of the present disclosure.

FIG. 3A depicts a block diagram of shared control system 200, in accordance with an embodiment of the present disclosure. The functionality represented by this block diagram is provided by one or more software modules including shared control module 134, other software modules 136, etc.

Generally, shared control system 200 performs complex surgical procedures collaboratively between robot 20 and the surgeon with the highest possible degree of autonomy, while ensuring safe operation at all times. In one sense, shared control system 200 is "self-aware" of the limitations of its automation capabilities.

Shared control system 200 includes manual control subsystem 210, autonomous control subsystem 220 and shared control subsystem 230. Also depicted in FIG. 3A is task space 2 including robot 20 and tissue 4. Tissue 4 may be one or more tissue samples, a region of interest of a patient, etc. Manual control subsystem 210 generates manual control command 212, which is input to shared control subsystem 230. Autonomous control subsystem 220 generates autonomous control command 222, which is input to shared control subsystem 230. Shared control subsystem 230 generates shared control command 232.

In the embodiment depicted in FIG. 3A, shared control command 232 is input to low level controller 240, which converts shared control command 232 to robot-specific control signal 231. Robot-specific control signal 231 is then sent to robot 20. For the embodiment including the KUKA LBR iiwa robot described above, low level controller 240 is a software module that is specific to this robot, such as the IIWA (Intelligent Industrial Work Assistant) Stack. In other embodiments, shared control command 232 may be sent directly to robot 20, which converts shared control command 232 to the appropriate robot-specific control signal.

Shared control subsystem 230 generates shared control command 232 according to the Equation 1:

$$U(t) = \alpha(t) \cdot M(t) + (1-\alpha(t)) \cdot A(t) \tag{1}$$

In Equation 1, manual control commands from the surgeon, $M(t)$, are combined with autonomous control commands, $A(t)$, using complementary scales $\alpha(t) \in [0, 1]$ and $1-\alpha(t)$, respectively, to form the shared control command to the robot, $U(t)$. The allocation function $\alpha(t)$ defines the respective percentages of the manual control command $M(t)$ and the autonomous control command $A(t)$ that are combined to form the shared control command $U(t)$. The allocation function $\alpha(t)$ defines these percentages with respect to an independent variable x that reflects or indicates certain performance criteria for the shared control subsystem 230. With respect to FIG. 3A, manual control command 212 represents $M(t)$, autonomous control command 222 represents $A(t)$, and shared control command 232 represents $U(t)$.

When $\alpha(t)$ is 0, the allocation function selects the autonomous control command as the shared control command. In other words, the shared control command is not influenced by the manual control command when $\alpha(t)$ is 0. Conversely, when $\alpha(t)$ is 1, the allocation function selects the manual control command as the shared control command. In other words, the shared control command is not influenced by the autonomous control command when $\alpha(t)$ is 1. When $\alpha(t)$ is a number between 0 and 1, the allocation function blends or combines the manual control command and the autonomous control command, based on the value of the allocation function, to generate the shared control command.

Figure 9:
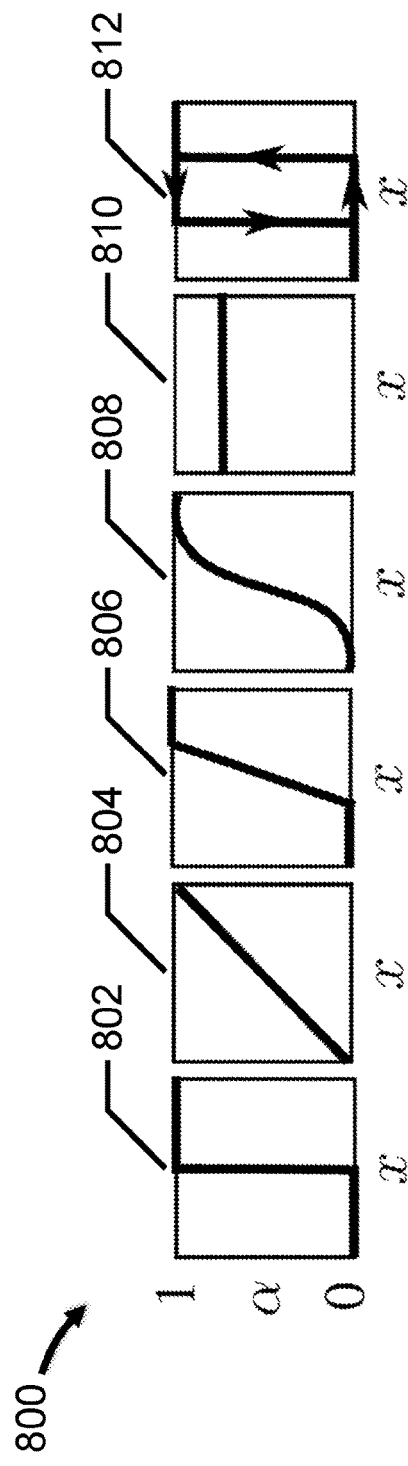
FIG. 9 depicts several allocation functions, in accordance with embodiments of the present disclosure.

Generally, the allocation function $\alpha(t)$ changes dynamically during the task and is a function of the independent variable x. Referring to FIG. 9, several allocation functions 800 are depicted, in accordance with embodiments of the present disclosure. Allocation function 802 is a function of tracking accuracy. Allocation function 804 is a function of proximity to obstacles and/or desired locations. Allocation function 806 is a function of the accuracy of predicting human intentions in controlling the robot. Allocation function 808 is a function of the level of manipulation precision. Allocation function 810 is a fixed function and does not change based on the performance criteria. Generally, performance criteria determine the confidence and hence the allocation function, which is task dependent. Allocation function 812 is a function of trust in the manual and/or autonomous control subsystems, and, more particularly, allocation function 812 is a function of the confidence in the manual and/or autonomous control subsystems and their dynamic uncertainties.

Generation of this confidence-based allocation function $\alpha(t)$ requires identification tests for both manual and autonomous control modes to reveal their respective strengths and weaknesses, and is described in more detail below. The factors affecting manual control mode performance include the angle of camera 40 and the dissimilarities between the kinematics of haptic device 30 and robot 20. The factors affecting autonomous control mode performance include random failures in detecting the desired cutting trajectory as well as any imprecision in the calculation of tool 24 location via the robot kinematic chain.

Figure 3B:
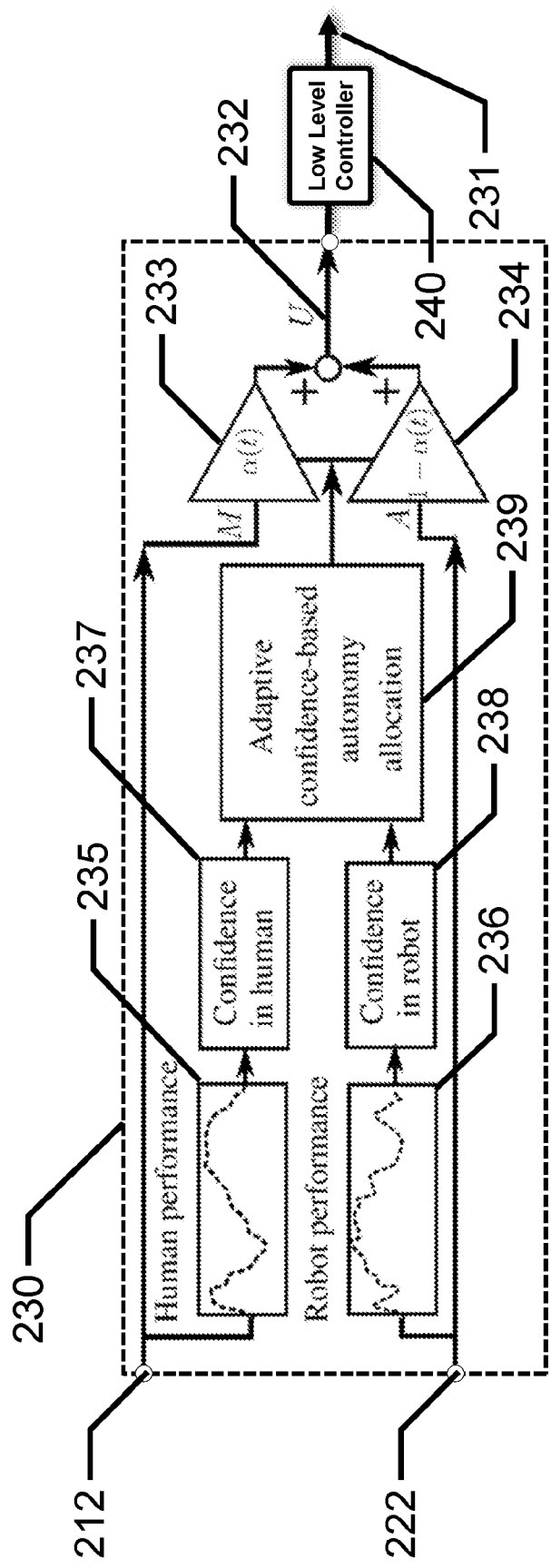
FIG. 3B depicts a block diagram of a shared control subsystem, in accordance with an embodiment of the present disclosure.

FIG. 3B depicts a block diagram of shared control subsystem 230, in accordance with an embodiment of the present disclosure. Also depicted in FIG. 3B is low level controller 240 which converts shared control command 232 into shared control signal 231. The functionality represented by this block diagram is provided by one or more software modules including shared control module 134, other software modules 136, etc.

Scale function 233 applies the allocation function $\alpha(t)$ to manual control command 212, and scale function 234 applies the allocation function $\alpha(t)$ to autonomous control command 222. The scaled commands are then combined to form shared control command 232.

Generation of the allocation function $\alpha(t)$ is based on manual confidence indicator 237 and autonomous confidence indicator 238. Manual confidence indicator 237 is determined based on manual tracking error data 235 that is acquired when processor 120 is operating in a manual control mode during performance of a predetermined task using tool 24. Manual tracking error data 235 are associated with the trajectory of tool 24 during performance of the predetermined task. Similarly, autonomous confidence indicator 238 is determined based on autonomous tracking error data 236 that are acquired when processor 120 is operating in an autonomous control mode during performance of the predetermined task using tool 24. The autonomous tracking error data 236 are associated with the trajectory of tool 24 during performance of the predetermined task. Performance of the predetermined task in manual control mode and autonomous control mode, in order to determine the manual and autonomous confidence indicators 237, 238, respectively, represents the identification tests noted above. This process is discussed in more detail below.

Figure 3C:
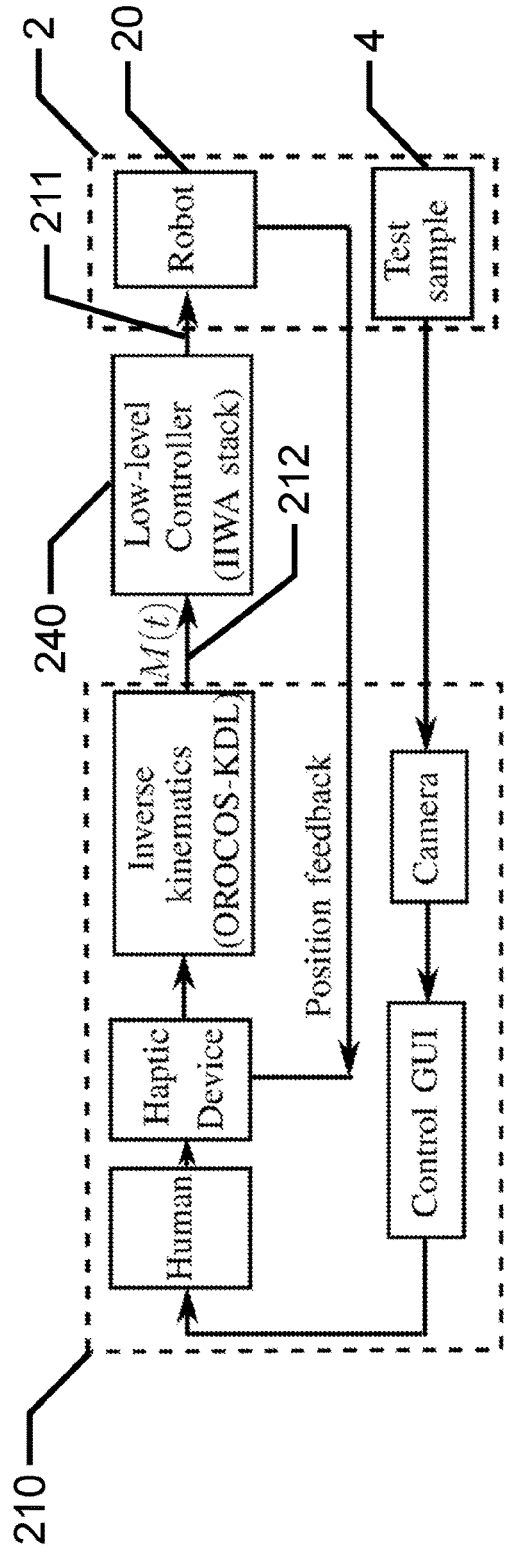
FIG. 3C depicts a block diagram of a manual control subsystem, in accordance with an embodiment of the present disclosure.

FIG. 3C depicts a block diagram of manual control subsystem 210, in accordance with an embodiment of the present disclosure. Also depicted in FIG. 3C are task space 2 including robot 20 and tissue 4, and low level controller 240 which converts manual control command 212 into manual control signal 211. The functionality represented by this block diagram is provided by one or more software modules including shared control module 134, other software modules 136, etc.

To perform a predetermined task in manual control mode, real-time video images from camera 40 are presented on display 50, and the surgeon plans the desired tool trajectory based on a reference trajectory inscribed on tissue 4, such as, for example, a circular pattern cut, and then follows the desired tool trajectory using haptic device 30. The position feedback from robot 20 and the position commands from haptic device 30 are used to determine reference positions of robot 20 in task space 2. In one embodiment, the initial position of robot 20 when the predetermined task starts is identified, and new reference positions read from the displacement of haptic device 30 are added to produce the final position of robot 20 in the Cartesian task-space. Inverse kinematics are applied to generate manual control command 212 in joint-space, and low level controller 240 then converts manual control command 212 to manual control signal 211. The manual control signal 211 is then sent to robot 20 over the appropriate I/O interface 140. In an alternative embodiment, the manual control command 212 is sent to robot 20 over the appropriate I/O interface 140, which processes the command as necessary.

Figure 3D:
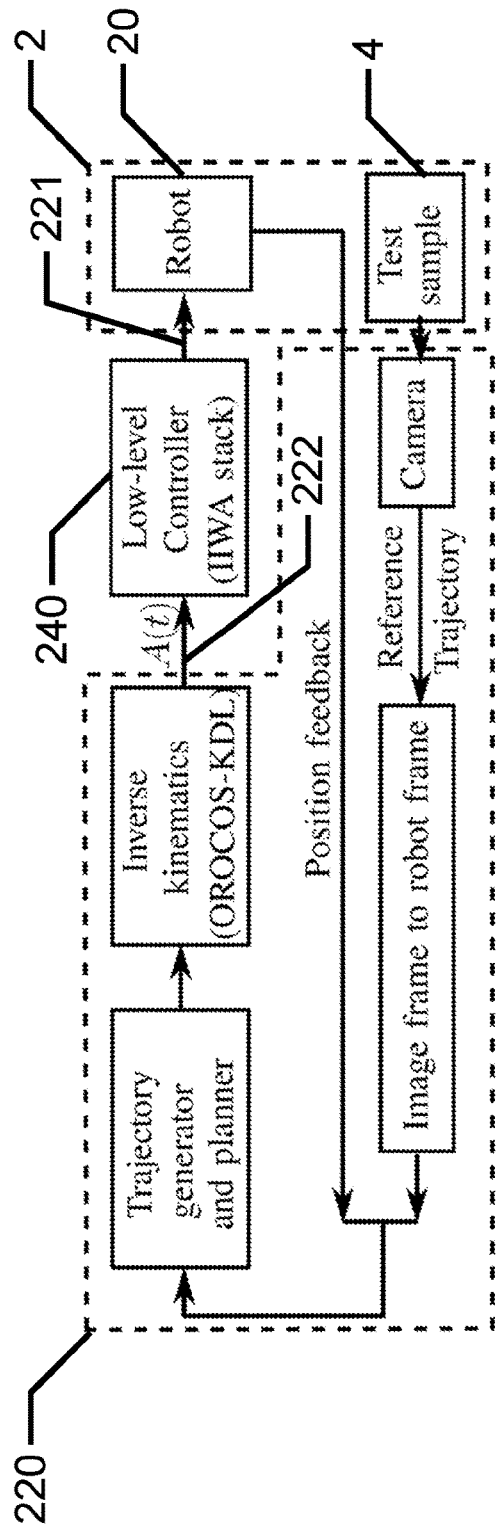
FIG. 3D depicts a block diagram of an autonomous control subsystem, in accordance with an embodiment of the present disclosure.

FIG. 3D depicts a block diagram of autonomous control subsystem 220, in accordance with an embodiment of the present disclosure. Also depicted in FIG. 3D are task space 2 including robot 20 and tissue 4, and low level controller 240 which converts autonomous control command 222 into autonomous control signal 221. The functionality represented by this block diagram is provided by one or more software modules including shared control module 134, other software modules 136, etc.

To perform a predetermined task in autonomous control mode, real-time video frames from camera 40 are processed to detect a reference trajectory inscribed on tissue 4, such as, for example, a circular pattern cut. Edge and contour detection algorithms in OpenCV are used to detect the reference cutting trajectory. Then, the reference trajectory is converted from the image frame to the Cartesian robot frame using a homography transformation. The resulting reference and the real-time positions of robot 20 are used in the trajectory generator and planner to produce multiple equidistant waypoints for the desired trajectory starting from the closest point on the desired trajectory to robot 20. Smooth, time-based desired trajectory segments are produced between the waypoints using, for example, Reflexxes Motion Libraries. Kinematics and Dynamics Library (KDL) in Open Robot Control Systems (OROCOS) may be used, for example, to transform the task-space trajectories of robot 20 to the joint-space trajectories and generate autonomous control command 222. Low level controller 240 then converts autonomous control command 222 to autonomous control signal 221.

Figure 4:
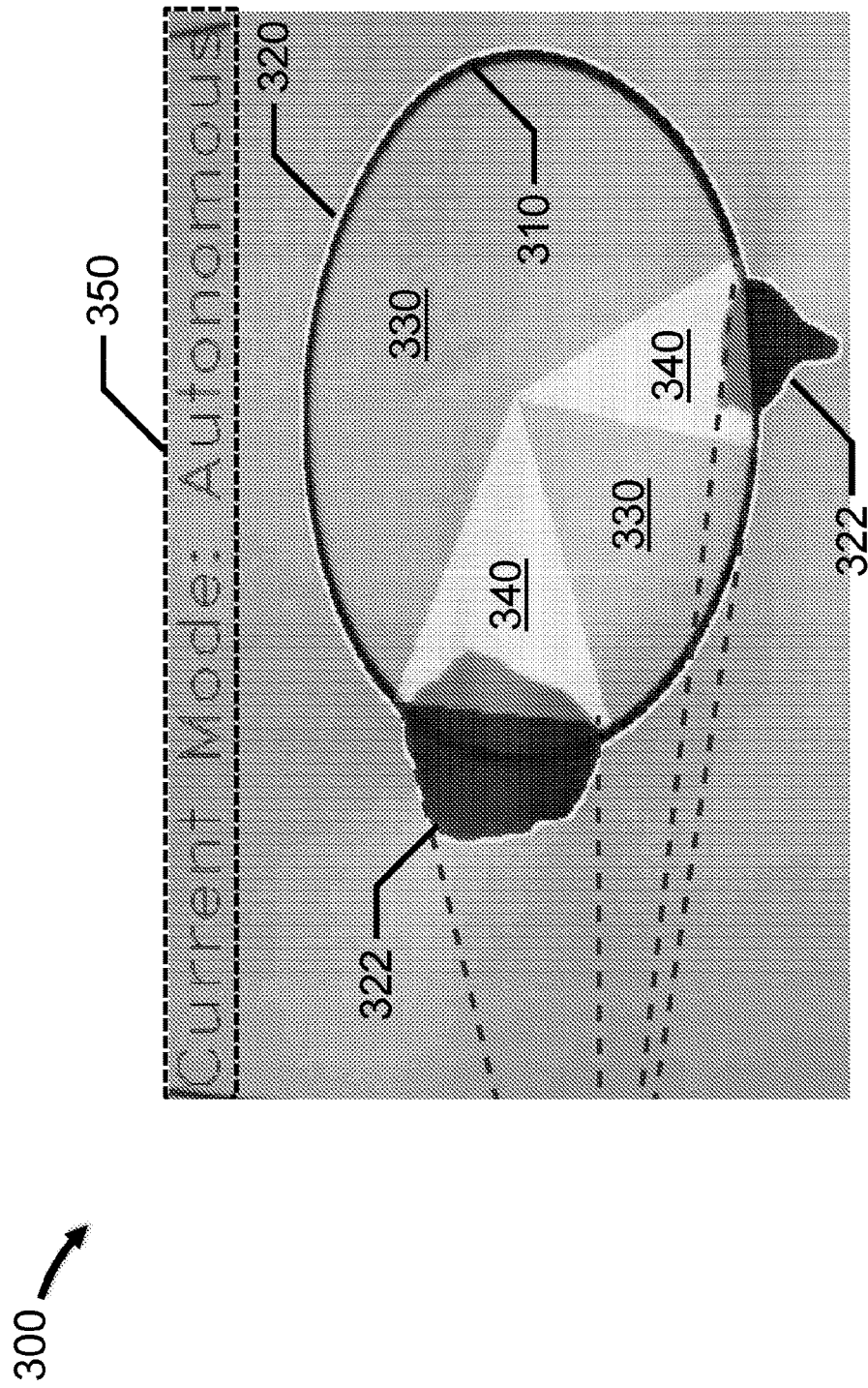
FIG. 4 depicts a graphical user interface for a shared control system, in accordance with an embodiment of the present disclosure.

FIG. 4 depicts a graphical user interface 300 for shared control system 200, in accordance with an embodiment of the present disclosure.

Graphical user interface (GUI) 300 depicts a video image of tissue 4 within task space 2, with reference trajectory 310 for the predetermined task inscribed thereon. GUI 300 also overlays a computer-generated image depicting desired trajectory 320 for the autonomous control mode, one or more suggested autonomous control mode regions 330, one or more suggested manual control mode regions 340, and control mode indicator 350. Suggested autonomous control mode regions 330 and suggested manual control mode regions 340 are determined based on the allocation function α(t). In certain embodiments, the shared control mode automatically switches between autonomous control mode and manual control mode based on the allocation function α(t) during the performance of the predetermined task. In other embodiments, the surgeon manually switches between the control modes, using haptic device 30, during the performance of the predetermined task.

Figure 5:
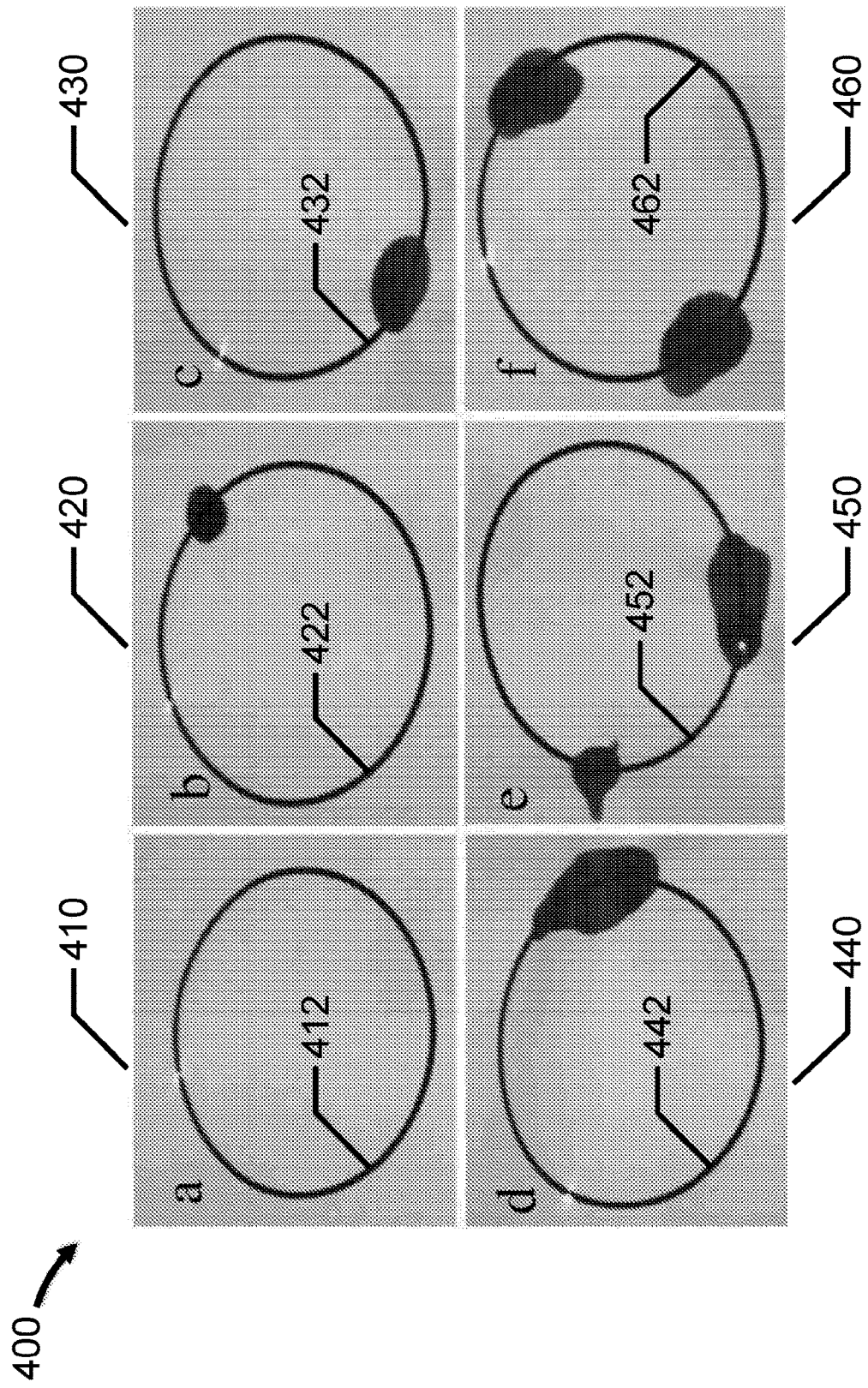
FIG. 5 illustrates a series of tissue samples, in accordance with an embodiment of the present disclosure.

FIG. 5 illustrates a series of tissue samples 400, in accordance with an embodiment of the present disclosure.

As discussed above, in order to determine manual confidence indicator 237 and autonomous confidence indicator 238, a predetermined task is first performed on different tissue samples in both manual control mode and autonomous control mode. In certain embodiments, the predetermined task is a circular pattern cut; other surgical procedures are also contemplated. Tissue samples 400 includes tissue sample 410 without pseudo-blood occlusions and with reference trajectory 412, tissue sample 420 with a small pseudo-blood occlusion and reference trajectory 422, tissue sample 430 with a medium pseudo-blood occlusion and reference trajectory 432, tissue sample 440 with a large pseudo-blood occlusion and reference trajectory 442, tissue sample 450 with a different size pseudo-blood occlusions and reference trajectory 452, and tissue sample 460 with symmetric, medium pseudo-blood occlusions and reference trajectory 462.

In certain embodiments, a laser pointer is attached to tool 24 and used to project a laser dot on tissue samples 400. Performance of the circular cut pattern on tissue samples 400 using a laser pointer attached to tool 24 sufficiently identifies the tracking accuracy of the autonomous and manual control modes. Tool 24 and attached laser pointer follow the desired cutting trajectory for each control mode for each tissue sample 400. In one embodiment, the motion of robot 20 was constrained to a plane parallel to the X-Y plane of tissue samples 400 at a fixed height and orientation to minimize laser-pointing inaccuracies.

In one embodiment, two identification tests are performed on each tissue sample 400. The first identification test performs the circular cut pattern on the tissue sample 400 under manual control mode, and the second identification test performs the circular cut pattern on the tissue sample under autonomous control mode. For each identification test, the actual trajectory of the laser dot is captured by camera 40, and the image data are processed to determine the tracking error of tool 24 by comparing the actual trajectory of the laser dot to the reference trajectory. In this embodiment, the laser dot and the location and size of any pseudo-blood occlusions are detected using functionality provided by the OpenCV library. Perspective transformations are applied to the image data to generate a top view of the laser dot trajectory, and then the image data is mapped to a new image frame that is a square 500×500 pixel plane. In this embodiment, each pixel represents 0.2 mm on the trajectory plane. The location of the laser dot is then tracked using color thresholding and blob detection, and the locations of any pseudo-blood occlusions in that tissue sample are similarly determined. The position of the laser dot is compared to the reference trajectory for that tissue sample, and the tracking error for that identification test is determined.

Figure 6:
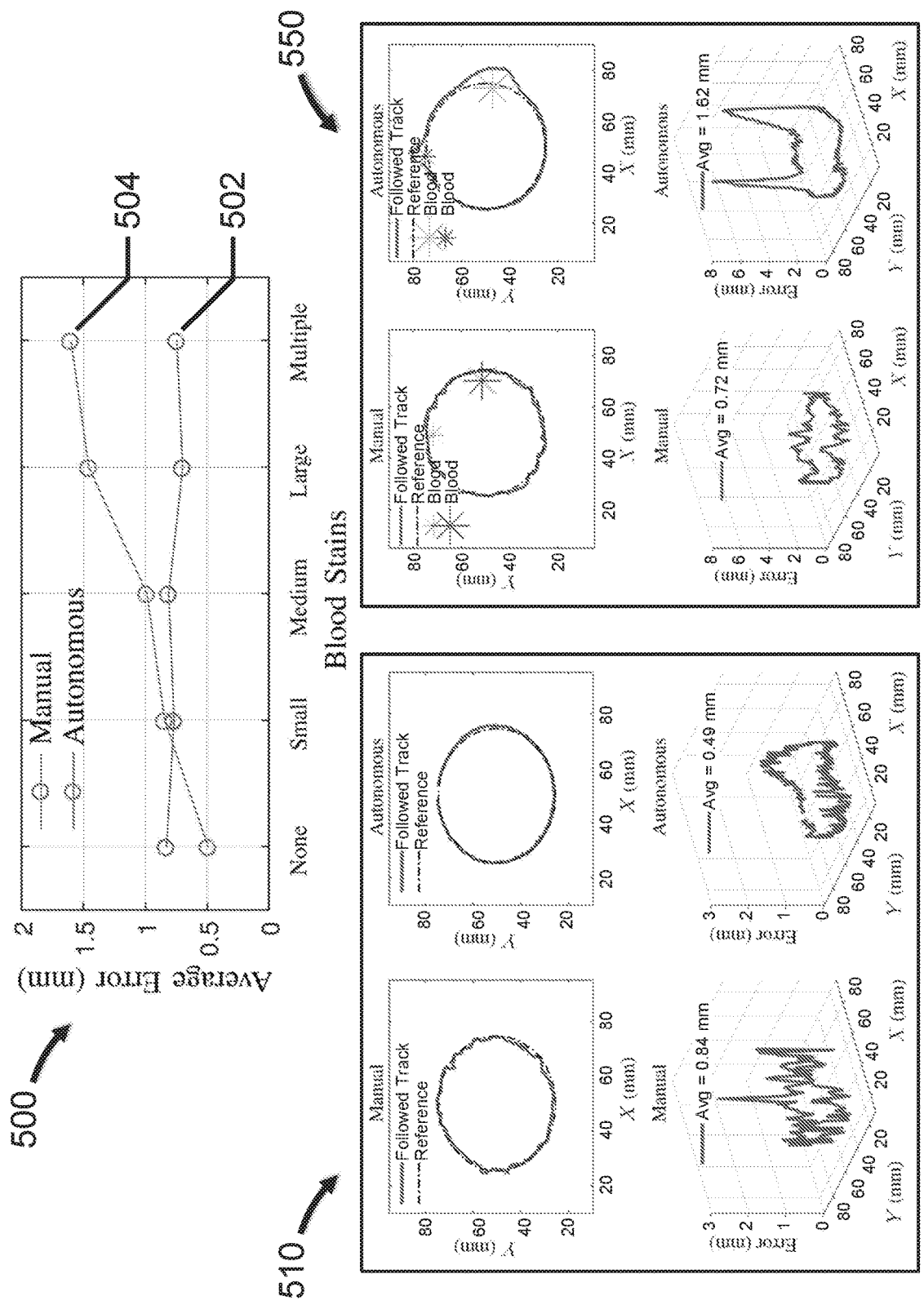
FIG. 6 depicts average tracking error graphs for tissue samples, in accordance with an embodiment of the present disclosure.

FIG. 6 depicts average tracking error graph 500 for tissue samples 400, in accordance with an embodiment of the present disclosure. Also depicted in FIG. 6 are tool trajectory and tracking error graphs 510 for tissue sample 410, and tool trajectory and tracking error graphs 550 for tissue sample 450.

Average tracking error graph 500 depicts average tracking error for manual control mode 502 and average tracking error for autonomous control mode 504 for identification tests performed on tissue sample 410, i.e., "none," tissue sample 420, i.e., "small," tissue sample 430, i.e., "medium," tissue sample 440, i.e., "large," and tissue samples 450, 460, i.e., "multiple."

Tissue sample 410 does not have pseudo-blood occlusions. Average tracking error graph 500 for tissue sample 410 indicate that the autonomous control mode outperforms the manual control mode—the average tracking error for the autonomous control mode was about 0.5 mm, while the average tracking error for the manual control mode was about 0.8 mm. However, as the complexity of the tissue sample increases due to the size and number of pseudo-blood occlusions, the average tracking error of the autonomous control mode increases from about 0.5 mm to about 1.6 mm, while the average tracking error of the manual control mode essentially remains within the same range for all of the samples, i.e., from about 0.6 mm to about 0.8 mm. More particularly, when pseudo-blood occlusions on the desired trajectory interferes with the detection algorithms of the autonomous control mode, the tracking error for the autonomous control mode locally increases near the pseudo-blood occlusions.

Tool trajectory and tracking error graphs 510 present more detailed data for tissue sample 410, including plots of the reference trajectory and the actual trajectory in the X-Y plane, and graphs of the trajectory tracking errors, for the manual control mode and the autonomous control mode. Tool trajectory and tracking error graphs 550 present more detailed data for tissue sample 450, including plots of the reference trajectory and the actual trajectory in the X-Y plane, and graphs of the trajectory tracking errors, for the manual control mode and the autonomous control mode. These data indicate that the local performance of the autonomous control mode on non-occluded regions of each desired trajectory is superior to the local of performance of the manual control mode on these regions. Conversely, the local performance of the manual control mode on occluded regions of each desired trajectory is superior to the local of performance of the autonomous control mode on these regions.

The shared control mode advantageously leverages the local performance strengths of both control modes to provide a more accurate control system by identifying confidence indicators for the autonomous control mode and the manual control mode in the vicinity of the occluded regions. The confidence indicators provide insight on how and when to switch the control modes to improve the overall task performance.

Figure 7:
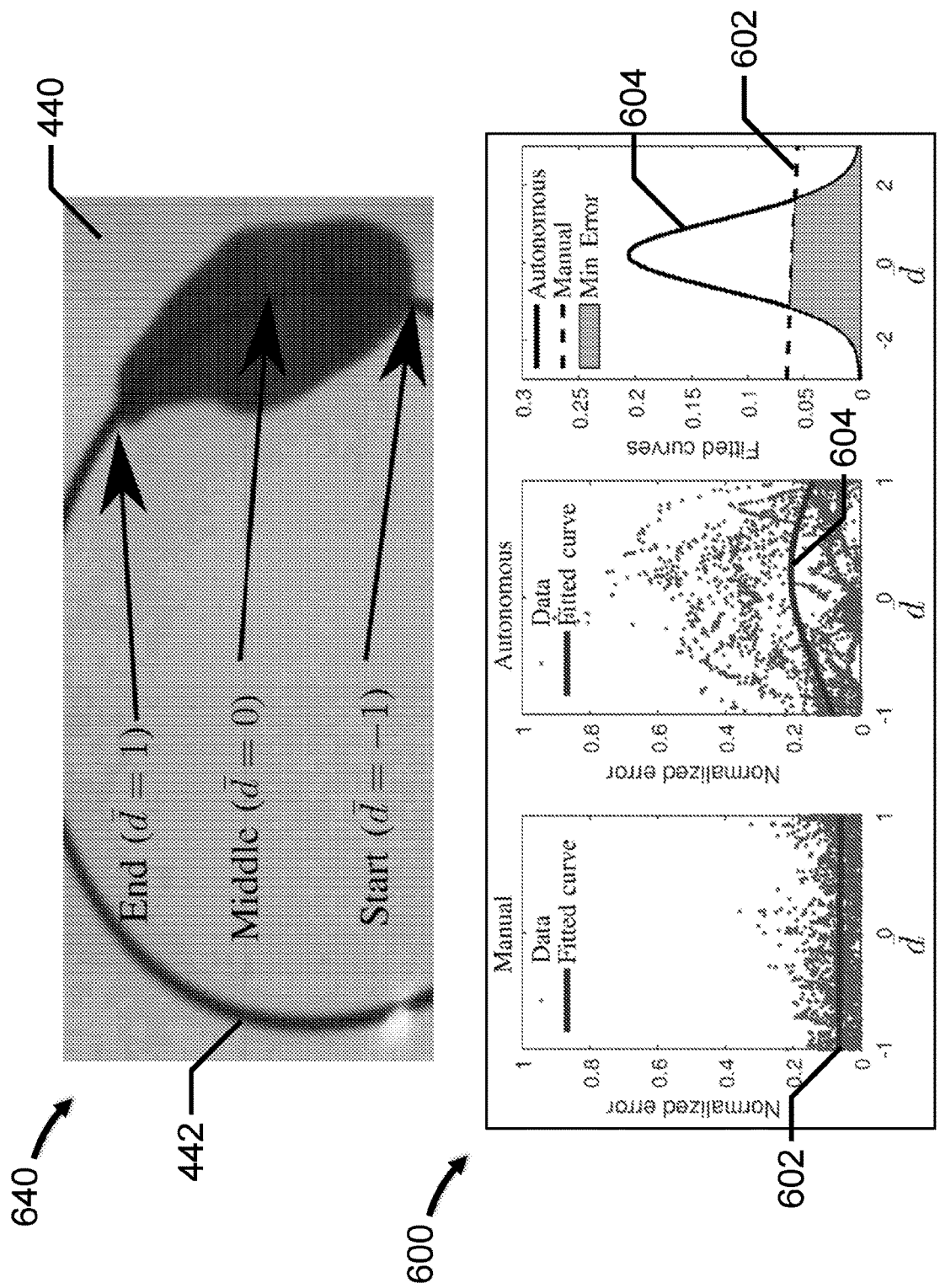
FIG. 7 depicts normalized tracking error graphs, in accordance with an embodiment of the present disclosure.

FIG. 7 depicts normalized tracking error graphs 600, in accordance with an embodiment of the present disclosure. FIG. 7 also depicts annotated tissue sample 640.

To determine the confidence indicators for the manual control mode and the autonomous control mode, in one embodiment, the tracking error data are normalized using a metric related to the size of the occlusion in each tissue sample 400. Other normalization metrics may also be used.

In this embodiment, the normalization metric, d, identifies the intersection of the reference trajectory with the pseudo-blood occlusion. Annotated tissue sample 640 depicts a portion of tissue sample 440 with reference trajectory 442, and several values for d. When approaching the pseudo-blood occlusion along the reference trajectory, the start of the pseudo-blood occlusion is defined as d=−1, the middle of the pseudo-blood occlusion is defined as d=0, and the end of the pseudo-blood occlusion is defined as d=1. Using these definitions, the intersection of the reference trajectory with pseudo-blood occlusions is normalized based on the size of the occlusion. In one embodiment, OpenCV blob detection algorithms are used to find the location and size of the pseudo-blood occlusions or blobs on the reference trajectory, and to normalize their intersections. The tracking error along d for each identification test was determined and normalized based on the blob sizes. Other blob detection algorithms are also contemplated.

The performances of autonomous control mode and the manual control mode, over all of the identification tests, are then analyzed based on the normalized proximity to the pseudo-blood occlusions. After the tracking error data is normalized for each control mode, a curve is fitted to each normalized control mode tracking error data set. In one example, the fitted curve for the manual control mode is a linear function, i.e., manual control mode curve 602, while the fitted curve for the autonomous control mode is a skewed Gaussian function, i.e., autonomous control mode curve 604. In this example, the fitted function for the manual control mode is governed by Equation 2, while the fitted function for the autonomous control mode is governed by Equation 3.

$$y_M = a_M d + b_M \quad (2)$$

with $a_M = -0.002$ and $b_M = 0.061$ $$y_A = a_A e^{-\left(\frac{d - b_A}{c_A}\right)^2} \quad (3)$$

with $a_A = 0.206$, $b_A = 0.213$, $c_A = 1.257$

Normalized tracking error graphs 600 include manual control mode normalized tracking error data, autonomous control mode normalized tracking error data, and the fitted curves for each data set.

These data suggest that the manual control mode is effective in pseudo-blood occlusion regions, while the autonomous control mode is more effective elsewhere. Based on these data, the confidence indicator for manual control mode is defined as $C_M = 1 - y_M$, and the confidence indicator for the autonomous control mode is defined as $C_A = 1 - y_A$.

Figure 8:
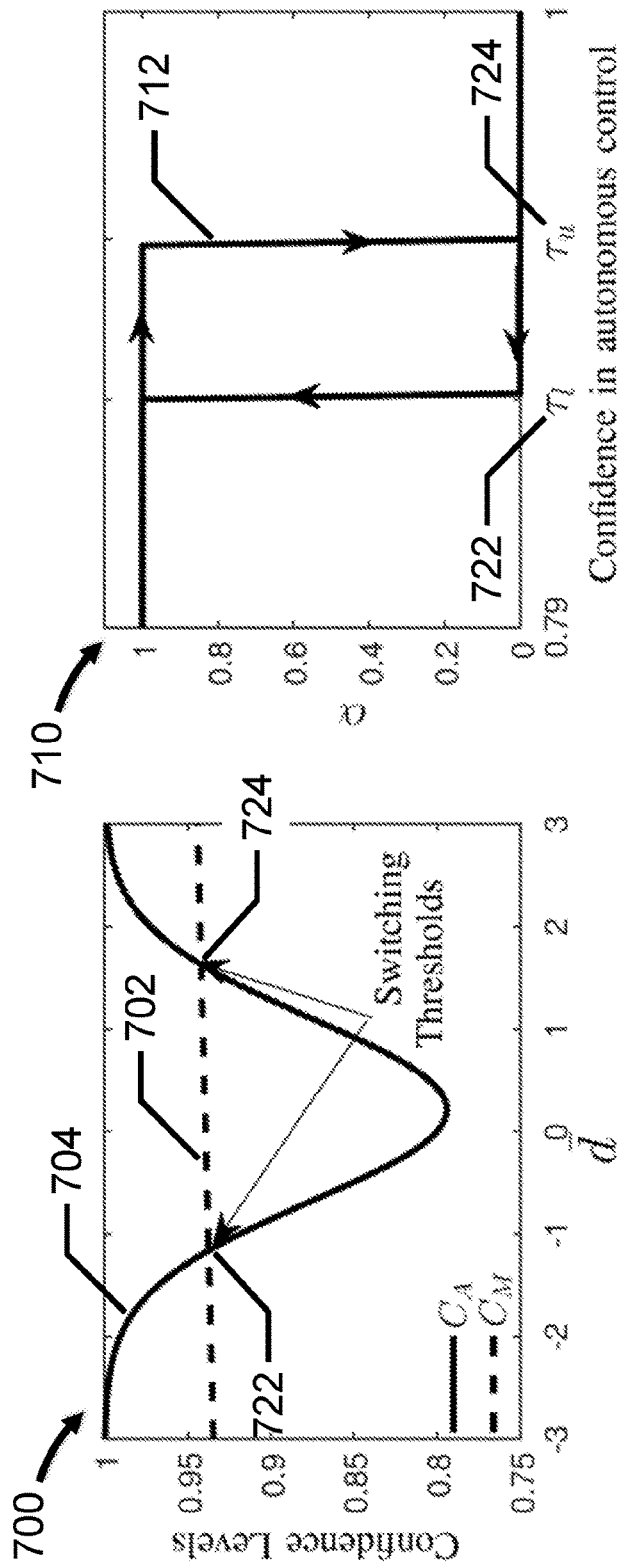
FIG. 8 depicts a confidence indicator graph and an allocation function graph, in accordance with an embodiment of the present disclosure.

FIG. 8 depicts confidence indicator graph 700 and allocation function graph 710, in accordance with an embodiment of the present disclosure.

Confidence indicator graph 700 depicts manual control mode confidence indicator 702 and autonomous control mode confidence indicator 704 for the experimental tests described above. After confidence indicators 702, 704 are determined, the allocation function α(t) is generated based on these confidence indicators. In one embodiment, confidence indicators 702, 704 are used to locally select the most reliable control mode as the predetermined task is performed. Because confidence indicator 702 is more or less constant, the allocation function α(t) and the decision thresholds for locally switching between manual control mode and autonomous control mode are determined based on confidence indicator 704.

Referring to the confidence indicator graph 700, as d approaches 0 from negative values, confidence indicator 704 is greater than confidence indicator 702. In other words, confidence in the autonomous control mode is greater than the manual control mode. As confidence indicator 704 gradually decreases from 1, a lower decision threshold, $T_{lower}$ 722, is reached at the point where confidence indicator 704 intersects confidence indicator 702 ($T_{lower}$=0.93 at d=−1.15). As the middle of the pseudo-blood occlusion is approached (d~0), confidence in the autonomous control mode reaches a minimum level ($T_{minimum}$ 0.79), and then begins to increase until upper decision threshold Tupper 724 is reached at the point where confidence indicator 704 intersects confidence indicator 702 ($T_{upper}$=0.94 at d=1.6). Between $T_{lower}$ 722 and $T_{upper}$ 724, confidence indicator 702 is greater than confidence indicator 704. In other words, confidence in the manual control mode is greater than the autonomous control mode. As d approaches positive values after $T_{upper}$ 724, confidence indicator 704 is greater than confidence indicator 702 and gradually increases back to 1. In other words, confidence in the autonomous control mode is again greater than the manual control mode.

Allocation function graph 710 depicts allocation function 712, which is a function of the confidence in the autonomous control mode, i.e., confidence indicator 704.

In this embodiment, allocation function 712 returns a value of 0 or 1 based on the value of confidence indicator 704. Referring to Equation 1, the value 0 indicates that the autonomous control mode has been selected for the shared control mode, and the value 1 indicates that the manual control mode has been selected for the shared control mode. In one example, the shared control mode is initially set to the autonomous control mode, and allocation function 712 has an initial setting of 0. As tool 24 approaches the beginning of a pseudo-blood occlusion in tissue 4, the normalized distance d approaches lower decision threshold $T_{lower}$ 722. When tool 24 crosses $T_{lower}$ 722, allocation function 712 returns the value 1, which changes the shared control mode to the manual control mode. As tool 24 approaches the end of the pseudo-blood occlusion in tissue 4, the normalized distance d approaches upper decision threshold $T_{upper}$ 724. When tool 24 crosses $T_{upper}$ 724, allocation function 712 returns the value 0, which changes the shared control mode back to the autonomous control mode.

Figure 10A:
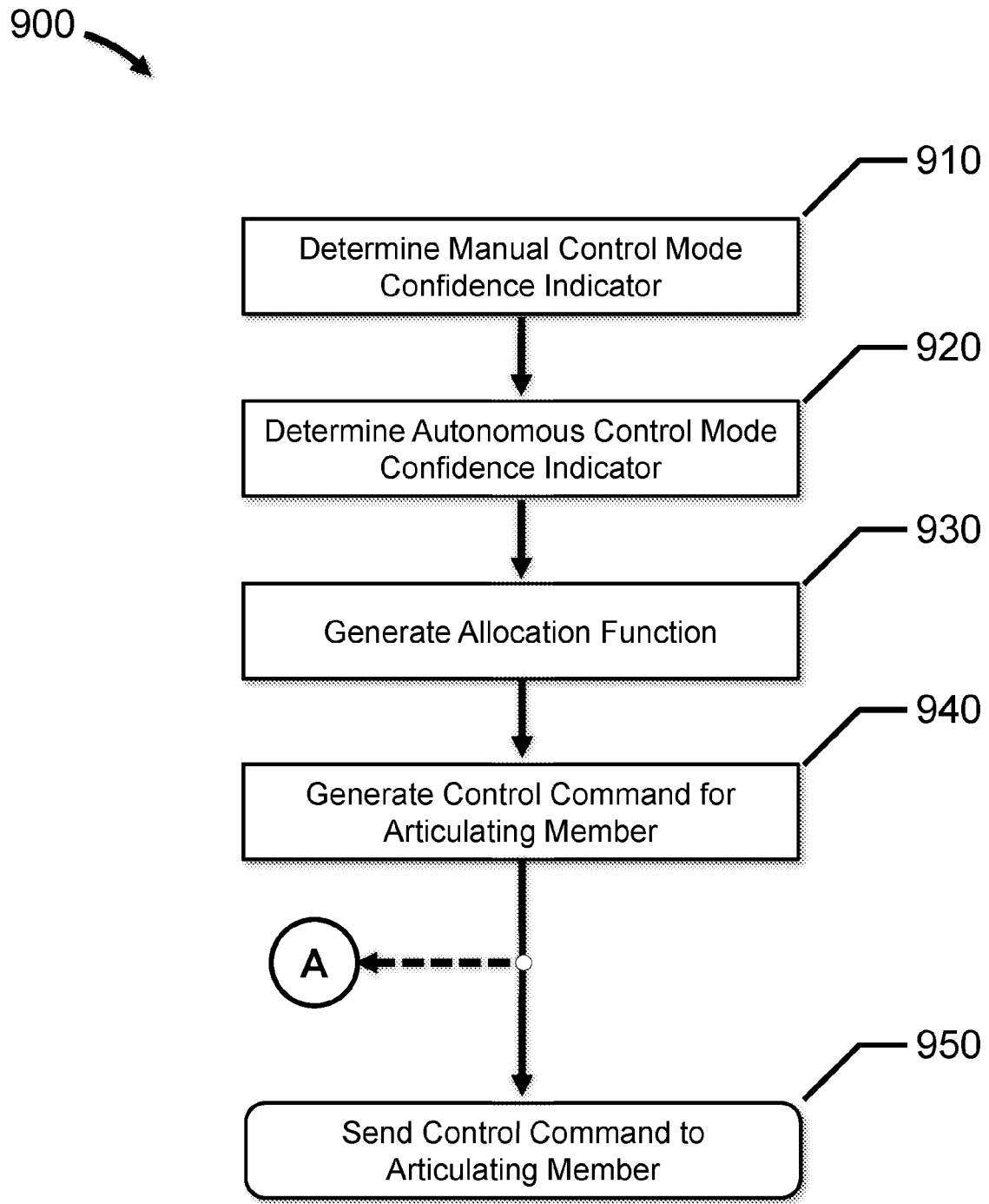
FIGS. 10A and 10B present flow diagrams depicting at least some of the functionality of the shared control module depicted in FIG. 2, in accordance with embodiments of the present disclosure.
Figure 10B:
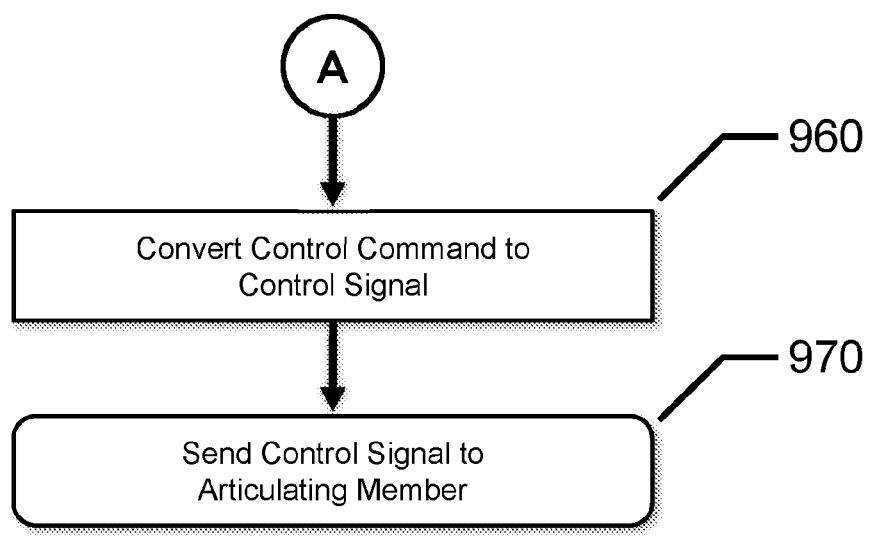

FIGS. 10A and 10B present flow diagrams depicting at least some of the functionality of shared control module 134 depicted in FIG. 2, in accordance with embodiments of the present disclosure FIG. 10A presents a flow diagram for controlling an articulating member including a tool, in accordance with an embodiment of the present disclosure.

At 910, a manual control mode confidence indicator is determined based on a manual control mode for the articulating member of the robot. As discussed above, tracking error data are acquired during the performance of a predetermined task under the manual control mode. The tracking error data represent the deviations between a reference trajectory and the actual trajectory of the tool. The manual control mode confidence indicator is determined based on this tracking error data. In one embodiment, the tracking error data may be normalized using a metric associated with the predetermined task, such as, for example, occlusion size, and then a curve may be fitted to the data to produce a normalized tracking error function. The manual control mode confidence indicator is then derived from the normalized tracking error function.

At 920, an autonomous control mode confidence indicator is determined based on an autonomous control mode for the articulating member of the robot. As discussed above, tracking error data are acquired during the performance of a predetermined task under the autonomous control mode. The tracking error data represent the deviations between a reference trajectory and the actual trajectory of the tool. The autonomous control mode confidence indicator is determined based on this tracking error data. In one embodiment, the tracking error data may be normalized using a metric associated with the predetermined task, such as, for example, occlusion size, and then a curve may be fitted to the data to produce a normalized tracking error function. The autonomous control mode confidence indicator is then derived from the normalized tracking error function.

At 930, an allocation function is generated based on the manual control mode confidence indicator and the autonomous control mode confidence indicator. As discussed above, the manual and autonomous control mode confidence indicators are used to locally select the most reliable control mode as the predetermined task is performed. For example, if the manual control mode confidence indicator is more or less constant, the allocation function α(t) and the decision thresholds for locally switching between manual control mode and autonomous control mode may be determined based on the autonomous control mode confidence indicator. Conversely, if the autonomous control mode confidence indicator is more or less constant, the allocation function α(t) and the decision thresholds for locally switching between manual control mode and autonomous control mode may be determined based on the manual control mode confidence indicator. In another example, the manual and autonomous control mode confidence indicators are blended to yield an allocation function α(t) that combines control commands from the manual control mode and control commands from the autonomous control mode.

At 940, a control command is generated for the articulating member of the robot based on the allocation function. As discussed above, when α(t) is 0, the autonomous control command A(t) is selected as the control command. In other words, the control command is not influenced by the manual control command when α(t) is 0. Conversely, when α(t) is 1, the manual control command M(t) is selected as the control command. In other words, the control command is not influenced by the autonomous control command when α(t) is 1. When α(t) is a number between 0 and 1, the manual control command and the autonomous control command are blended, based on the value of the allocation function α(t), to generate the control command. As discussed above, the allocation function α(t) changes as a function of the independent variable x. For example, the independent variable x may be the confidence in the autonomous control mode, as discussed above.

At 950, the control command is sent to the articulating member. As discussed above, in one embodiment, the control command is input to a low level controller, which converts the control command to a robot-specific control signal. The robot-specific control signal is then sent to the robot over the appropriate I/O Interface. In another embodiment, the control command is sent directly to the robot, which converts the control command to the appropriate robot-specific control signal.

FIG. 10B presents a flow diagram for controlling an articulating member including a tool, in accordance with an embodiment of the present disclosure.

At 960, the control command is converted to a robot-specific control signal, as discussed above.

At 970, the control signal is sent to the articulating member, as discussed above.

INDUSTRIAL APPLICABILITY

The present disclosure is susceptible and capable of industrial application because it can be made and used in the medical device and medical services industries, which are both useful and practical arts. However, the present disclosure is not limited to these industries; to the contrary, the present disclosure is applicable to any industry in which improved control of a robot executing a predetermined task is desired.

One embodiment of the present disclosure provides a system that includes an articulating member and a computer coupled to the articulating member. The articulating member includes a tool, and the computer includes a processor. The processor is configured to determine a first confidence indicator based on a manual control mode for the articulating member, determine a second confidence indicator based on an autonomous control mode for the articulating member, generate an allocation function based on the first confidence indicator and the second confidence indicator, and generate a control command for the articulating member based on the allocation function.

In another embodiment, the first confidence indicator is based on first data acquired when the processor is operating in the manual control mode during a first performance of a predetermined task using the tool, and the first data include manual tracking error data associated with a first trajectory of the tool during the first performance of the predetermined task.

In another embodiment, the second confidence indicator is based on second data acquired when the processor is operating in the autonomous control mode during a second performance of the predetermined task, and the second data include autonomous tracking error data associated with a second trajectory of the tool during the second performance of the predetermined task.

In another embodiment, when the processor is operating in a shared control mode to perform the predetermined task using the tool, the processor is further configured to generate a manual control command for the articulating member based on input data received from an input device coupled to the processor, generate an autonomous control command for the articulating member, generate the control command based on the allocation function, the autonomous control command and the manual control command, convert the control command into a robot-specific control signal, and send the robot-specific control signal to the articulating member.

In another embodiment, the allocation function selects either the manual control command or the autonomous control command as the control command.

In another embodiment, the allocation function defines at least one decision threshold and determines whether the manual control command or the autonomous control command is selected as the control command.

In another embodiment, the control command is a combination of the manual control command and the autonomous control command, and the allocation function defines respective percentages of the manual control command and the autonomous control command.

In another embodiment, the processor is further configured to provide a graphical user interface (GUI) on a display coupled to the processor, the GUI including an image of a work space in which the predetermined task is performed, a desired trajectory of the tool for the predetermined task, at least one manual control mode region along the desired trajectory, and at least one autonomous control mode region along the desired trajectory.

In another embodiment, the processor is further configured to receive, from the input device, a user selection of either the manual control command or the autonomous control command as the control command.

In another embodiment, the predetermined task is a two dimensional pattern cutting surgical task.

The embodiments described above are combinable.

A further embodiment of the present disclosure provides a method for controlling an articulating member including a tool. The method includes determining a first confidence indicator based on a manual control mode for the articulating member, determining a second confidence indicator based on an autonomous control mode for the articulating member, generating an allocation function based on the first confidence indicator and the second confidence indicator, generating a control command for the articulating member based on the allocation function, and sending the control command to the articulating member.

In another further embodiment, the first confidence indicator is based on first data acquired when operating in the manual control mode during a first performance of a predetermined task using the tool, the first data include manual tracking error data associated with a first trajectory of the tool during the first performance of the predetermined task, the second confidence indicator is based on second data acquired when operating in the autonomous control mode during a second performance of the predetermined task, and the second data include autonomous tracking error data associated with a second trajectory of the tool during the second performance of the predetermined task.

In another further embodiment, when operating in a shared control mode to perform the predetermined task using the tool, the method further comprises generating a manual control command for the articulating member based on input data received from an input device, generating an autonomous control command for the articulating member, generating the control command is based on the allocation function, the autonomous control command and the manual control command, converting the control command into a robot-specific control signal, and sending the robot-specific control signal to the articulating member.

In another further embodiment, the allocation function selects either the manual control command or the autonomous control command as the control command, and the allocation function defines at least one decision threshold and determines whether the manual control command or the autonomous control command is selected as the control command.

In another further embodiment, the control command is a combination of the manual control command and the autonomous control command, and the allocation function defines respective proportions of the manual control command and the autonomous control command.

The further embodiments described above are combinable.

While implementations of the disclosure are susceptible to embodiment in many different forms, there is shown in the drawings and will herein be described in detail specific embodiments, with the understanding that the present disclosure is to be considered as an example of the principles of the disclosure and not intended to limit the disclosure to the specific embodiments shown and described. In the description above, like reference numerals may be used to describe the same, similar or corresponding parts in the several views of the drawings.

In this document, relational terms such as first and second, top and bottom, and the like may be used solely to distinguish one entity or action from another entity or action without necessarily requiring or implying any actual such relationship or order between such entities or actions. The terms "comprises," "comprising," "includes," "including,"

"has," "having," or any other variations thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

Reference throughout this document to "one embodiment," "certain embodiments," "an embodiment," "implementation(s)," "aspect(s)," or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; B and C; A, B and C." An exception to this definition will occur only when a combination of elements, functions, steps or acts are in some way inherently mutually exclusive. Also, grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth. References to items in the singular should be understood to include items in the plural, and vice versa, unless explicitly stated otherwise or clear from the text.

Recitation of ranges of values herein are not intended to be limiting, referring instead individually to any and all values falling within the range, unless otherwise indicated, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," "for example," or the like) provided herein, is intended merely to better illuminate the embodiments and does not pose a limitation on the scope of the embodiments. No language in the specification should be construed as indicating any unclaimed element as essential to the practice of the embodiments.

For simplicity and clarity of illustration, reference numerals may be repeated among the figures to indicate corresponding or analogous elements. Numerous details are set forth to provide an understanding of the embodiments described herein. The embodiments may be practiced without these details. In other instances, well-known methods, procedures, and components have not been described in detail to avoid obscuring the embodiments described. The description is not to be considered as limited to the scope of the embodiments described herein.

In the following description, it is understood that terms such as "first," "second," "top," "bottom," "up," "down," "above," "below," and the like, are words of convenience and are not to be construed as limiting terms. Also, the terms apparatus, device, system, etc. may be used interchangeably in this text.

The many features and advantages of the disclosure are apparent from the detailed specification, and, thus, it is intended by the appended claims to cover all such features and advantages of the disclosure which fall within the scope of the disclosure. Further, since numerous modifications and variations will readily occur to those skilled in the art, it is not desired to limit the disclosure to the exact construction and operation illustrated and described, and, accordingly, all suitable modifications and equivalents may be resorted to that fall within the scope of the disclosure.

What is claimed is:

1. A system, comprising:
an articulating member including a tool; and
a computer, coupled to the articulating member, including a processor configured to:
determine a first confidence indicator based on a manual control mode for the articulating member,
determine a second confidence indicator based on an autonomous control mode for the articulating member,
generate an allocation function based on the first confidence indicator and the second confidence indicator, and
generate a control command for the articulating member based on the allocation function,
wherein the first confidence indicator is based on first data acquired when the processor is operating in the manual control mode during a first performance of a predetermined task using the tool,
wherein the first data include manual tracking error data associated with a first trajectory of the tool during the first performance of the predetermined task,
wherein the second confidence indicator is based on second data acquired when the processor is operating in the autonomous control mode during a second performance of the predetermined task, and
wherein the second data include autonomous tracking error data associated with a second trajectory of the tool during the second performance of the predetermined task.

2. The system according to claim 1, where, when the processor is operating in a shared control mode to perform the predetermined task using the tool, the processor is further configured to:
generate a manual control command for the articulating member based on input data received from an input device coupled to the processor;
generate an autonomous control command for the articulating member;
generate the control command based on the allocation function, the autonomous control command and the manual control command;
convert the control command into a robot-specific control signal; and
send the robot-specific control signal to the articulating member.

3. The system according to claim 2, where the allocation function selects either the manual control command or the autonomous control command as the control command.

4. The system according to claim 3, where the allocation function defines at least one decision threshold and determines whether the manual control command or the autonomous control command is selected as the control command.

5. The system according to claim 2, where the control command is a combination of the manual control command and the autonomous control command, and the allocation function defines respective percentages of the manual control command and the autonomous control command.

6. The system according to claim 2, where the processor is further configured to provide a graphical user interface (GUI) on a display coupled to the processor, the GUI including an image of a work space in which the predetermined task is performed, a desired trajectory of the tool for the predetermined task, at least one manual control mode region along the desired trajectory, and at least one autonomous control mode region along the desired trajectory.

7. The system according to claim 6, where the processor is further configured to receive, from the input device, a user selection of either the manual control command or the autonomous control command as the control command.

8. The system according to claim 1, where the predetermined task is a two-dimensional pattern cutting surgical task.

9. A method for controlling an articulating member including a tool, the method comprising:
   determining a first confidence indicator based on a manual control mode for the articulating member;
   determining a second confidence indicator based on an autonomous control mode for the articulating member;
   generating an allocation function based on the first confidence indicator and the second confidence indicator;
   generating a control command for the articulating member based on the allocation function; and
   sending the control command to the articulating member,
   wherein the first confidence indicator is based on first data acquired when operating in the manual control mode during a first performance of a predetermined task using the tool;
   wherein the first data include manual tracking error data associated with a first trajectory of the tool during the first performance of the predetermined task;
   wherein the second confidence indicator is based on second data acquired when operating in the autonomous control mode during a second performance of the predetermined task; and
   wherein the second data include autonomous tracking error data associated with a second trajectory of the tool during the second performance of the predetermined task.

10. The method according to claim 9, where, when operating in a shared control mode to perform the predetermined task using the tool, the method further comprises:
    generating a manual control command for the articulating member based on input data received from an input device;
    generating an autonomous control command for the articulating member;
    generating the control command is based on the allocation function, the autonomous control command and the manual control command;
    converting the control command into a robot-specific control signal; and
    sending the robot-specific control signal to the articulating member.

11. The method according to claim 10, where the allocation function selects either the manual control command or the autonomous control command as the control command, and the allocation function defines at least one decision threshold and determines whether the manual control command or the autonomous control command is selected as the control command.

12. The method according to claim 10, where the control command is a combination of the manual control command and the autonomous control command, and the allocation function defines respective proportions of the manual control command and the autonomous control command.

13. The method according to claim 10, further comprising:
    providing a graphical user interface (GUI) on a display, the GUI including an image of a work space in which the predetermined task is performed, a desired trajectory of the tool for the predetermined task, at least one manual control mode region along the desired trajectory, and at least one autonomous control mode region along the desired trajectory.

14. The method according to claim 13, further comprising:
    receiving, from the input device, a user selection of either the manual control command or the autonomous control command as the control command.

15. The method according to claim 9, where the predetermined task is a two-dimensional pattern cutting surgical task.

16. A method for controlling a robot including a tool, the method comprising:
    controlling the tool to follow a first trajectory using a haptic device on a manual control mode for the robot;
    determining a first confidence indicator based on the manual control mode for the robot, wherein the first confidence indicator is based on first data acquired when operating in the manual control mode during a first performance of a predetermined task using the tool, wherein the first data include manual tracking error data associated with the first trajectory of the tool;
    controlling the tool to follow a second trajectory on an autonomous control mode for the robot;
    determining a second confidence indicator based on the autonomous control mode for the robot, wherein the second confidence indicator is based on second data acquired when operating in the autonomous control mode wherein the second data include autonomous tracking error data associated with the second trajectory of the tool;
    generating an allocation function based on the first confidence indicator and the second confidence indicator, wherein the allocation function comprises a function of tracking accuracy;
    generating a control command for the robot based on the allocation function; and
    sending the control command to the robot.

17. The method of claim 16, wherein the manual tracking error data associated with the first trajectory of the tool comprise a first difference between the first trajectory and a first performed trajectory of the tool to follow the first trajectory, and
    wherein the autonomous tracking error data associated with the second trajectory of the tool comprise a second difference between the second trajectory and a second performed trajectory of the tool to follow the second trajectory.

18. The method of claim 17, wherein the function of tracking accuracy comprises a function of the first confidence indicator and the second confidence indicator.

* * * * *